(12) United States Patent
Tumlinson et al.

(10) Patent No.: US 11,806,277 B2
(45) Date of Patent: Nov. 7, 2023

(54) INTRAVITREAL INJECTION DEVICE WITH COMBINED VITREOUS SAMPLING

(71) Applicant: Twenty Twenty Therapeutics LLC, South San Francisco, CA (US)

(72) Inventors: Alexandre Tumlinson, South San Francisco, CA (US); Ellen Kaplan, South San Francisco, CA (US)

(73) Assignee: TWENTY TWENTY THERAPEUTICS LLC, South San Francisco, CA (US)

( * ) Notice: Subject to any disclaimer, the term of this patent is extended or adjusted under 35 U.S.C. 154(b) by 226 days.

(21) Appl. No.: 17/319,742

(22) Filed: May 13, 2021

(65) Prior Publication Data

US 2021/0353455 A1    Nov. 18, 2021

Related U.S. Application Data

(60) Provisional application No. 63/024,725, filed on May 14, 2020.

(51) Int. Cl.
*A61F 9/00* (2006.01)
*A61M 5/315* (2006.01)
(Continued)

(52) U.S. Cl.
CPC ........ *A61F 9/0008* (2013.01); *A61F 9/00736* (2013.01); *A61F 9/00781* (2013.01);
(Continued)

(58) Field of Classification Search
CPC ............... A61F 9/0008; A61F 9/00736; A61F 9/00781; A61M 5/19; A61M 5/31501;
(Continued)

(56) References Cited

U.S. PATENT DOCUMENTS

| 4,795,423 A * | 1/1989 | Osterholm | ........... A61K 9/0029 604/521 |
| 2009/0196903 A1 * | 8/2009 | Kliman | ................... A61P 27/02 424/423 |

(Continued)

OTHER PUBLICATIONS

Saxena, S., Lai, T.Y., Koizumi, H. et al., "Anterior chamber paracentesis during intravitreal injections in observational trials: effectiveness and safety and effects." International Journal of Retina and Vitreous (2019) 5 pages.

*Primary Examiner* — Dung T Ulsh
(74) *Attorney, Agent, or Firm* — TAROLLI, SUNDHEIM, COVELL & TUMMINO L.L.P.

(57) ABSTRACT

An ophthalmic device includes a housing configured to hold an injectant chamber configured to store an injectant, a plunger disposed within the injectant chamber, and a stopper coupled to a distal portion of the plunger. The device also includes a hypodermic needle disposed at a distal end of the housing, and a sample chamber located within the housing adjacent to the distal end. The housing, hypodermic needle, and sample chamber are arranged such that when the stopper is moved to a first depth within the housing, the sample chamber is configured to receive material via the hypodermic needle. The housing, hypodermic needle, and sample chamber are also arranged such that when the stopper is moved to a second depth within the housing exceeding the first depth, the injectant chamber is configured to dispense the injectant through the hypodermic needle.

17 Claims, 14 Drawing Sheets

(51) Int. Cl.
    *A61M 5/19*         (2006.01)
    *A61M 5/32*         (2006.01)
    *A61F 9/007*       (2006.01)
    *A61M 5/31*         (2006.01)

(52) U.S. Cl.
    CPC .......... *A61M 5/19* (2013.01); *A61M 5/31501* (2013.01); *A61M 5/32* (2013.01); *A61M 2005/3126* (2013.01); *A61M 2210/0612* (2013.01)

(58) Field of Classification Search
    CPC ............ A61M 5/32; A61M 2005/3126; A61M 2210/0612
    See application file for complete search history.

(56) References Cited

U.S. PATENT DOCUMENTS

| | | | |
|---|---|---|---|
| 2009/0318856 A1* | 12/2009 | Glaser | A61B 10/0045 604/35 |
| 2019/0159930 A1* | 5/2019 | Ang | A61M 5/3202 |
| 2020/0179606 A1* | 6/2020 | Weinstein | A61M 5/31578 |
| 2020/0390596 A1* | 12/2020 | Chalberg, Jr. | A61M 5/20 |
| 2021/0353456 A1* | 11/2021 | Rotenstreich | A61F 9/009 |

* cited by examiner

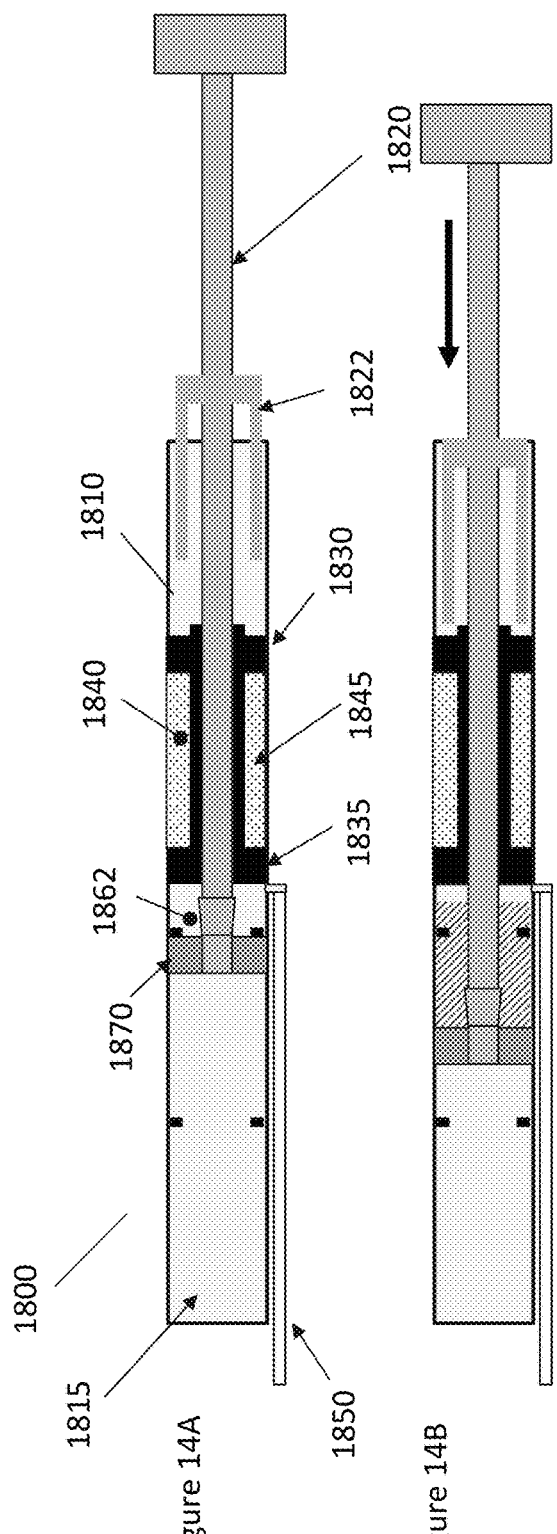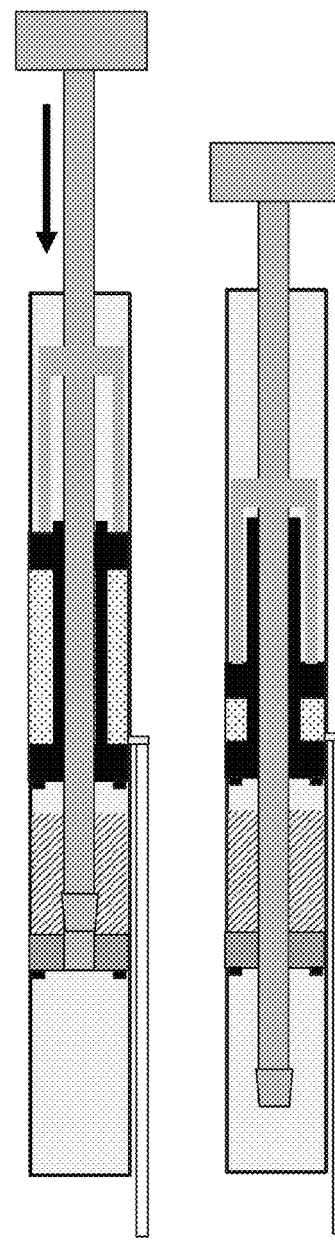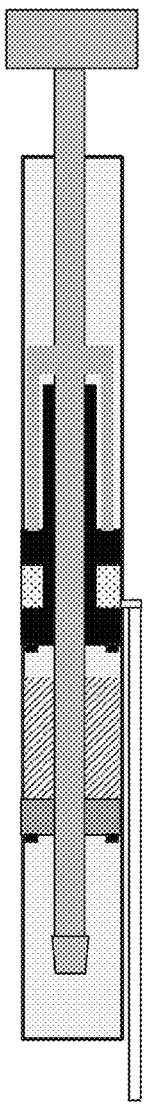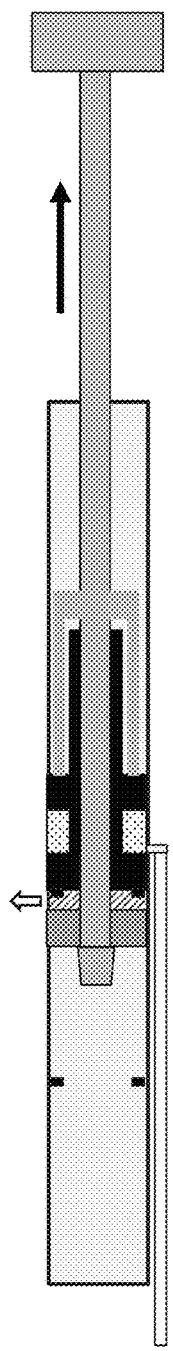
Figure 14A  Figure 14B  Figure 14C  Figure 14D  Figure 14E

INTRAVITREAL INJECTION DEVICE WITH COMBINED VITREOUS SAMPLING

CROSS-REFERENCE TO RELATED APPLICATIONS

The present application claims priority to and the benefit of U.S. Provisional Application No. 63/024,725, filed May 14, 2020, the entirety of which is incorporated by reference.

TECHNICAL FIELD

The subject matter described herein relates to devices, systems, and methods for injection of substances into, and sampling of, aqueous and vitreous humors of the eye. The disclosed intravitreal injection and sampling device has particular but not exclusive utility for diagnosis and treatment of ophthalmic disorders in humans.

BACKGROUND

Vitreous humor is a colorless, gelatinous fluid within an eye or eyeball of humans or other vertebrates composed of approximately 98-99% water with trace amounts of hyaluronic acid, glucose, anions, cations, ions, and a fine network of collagen. Vitreous humor provides support to the surrounding structures of the eye, absorbs mechanical trauma, and provides circulation and regulation of oxygen, metabolites and nutrients. It is produced largely by cells of the ciliary body. Changes in vitreal structure that occur with aging, are important in the pathogenesis of many vitreoretinal diseases.

Intraocular pressure (TOP) quantifies the pressure of the vitreous humor inside the eye. Many individuals suffer from disorders, such as glaucoma, that cause chronic heightened TOP. Over time, heightened TOP can cause damage to the optical nerve of the eye, leading to loss of vision. An TOP increase of 2 mmHg may be considered pathological and indicative of glaucoma.

Presently, treatment of ophthalmic disorders mainly involves periodically administering pharmaceutical agents to the eye. These drugs can be delivered by, for example, intravitreal injection. Intravitreal injection is one of the most common procedures performed in ophthalmology today. A variety of drugs are delivered directly to the clear vitreous gel that supports the globe of the eye. These drugs act directly in the vitreous or in the surrounding retinal tissues over the following months. For example, intravitreal injection is a common route of delivery for vascular endothelial growth factor inhibiting (anti-VEGF) proteins, which are highly potent compounds tolerated at high doses, with intravitreal half-lives about one week. Anti-VEGF biologics and steroids are the most commonly administered drugs by this route. These drugs may be administered on a chronic basis.

One recommended procedure for intravitreal injection includes preparation of an injection needle, topical anesthesia and disinfection of the eye surface, holding the eye open with a lid speculum or other means, optional lateral dislocation of the conjunctiva at the injection site, and insertion of the needle a few mm lateral to the limbus to approximately the full depth of the needle, injecting the drug, withdrawing the needle, and allowing the conjunctiva to cover the injection site. Post injection care typically includes a basic verification of functional vision such as requesting the patient to count the number of fingers shown by the doctor. This functional test verifies that acute IOP increase due to injection has not impacted the optic nerve head in a way that requires immediate relief.

Another important ophthalmic procedure is vitreous sampling. Vitreous sampling may inform various aspects of eye care. Samples of vitreous may be analyzed for cellular content and extracellular structure by histology, or immunologic analysis. Histology can, for example, provide a definitive diagnosis for the type of infection causing a endophthalmitis. Identification of the type of immune cells present and the immune mediator proteins expressed may inform the treatment of uveitis. Identification of the amount of VEGF present in the vitreous may give an indication of how likely imminent neovascularization is to occur, or how likely it is that VEGF compounds are responsible for an observed case of neovascularization. Non-responders to anti-VEGF treatment remains one of the most troublesome aspects of treating neovascularization in exudative, age-related vascular degeneration (also known as wet AMD) and diabetic retinopathy.

Two common methods of vitreous sampling—with a cutter, or with needle aspiration—appear to be approximately equivalent for the purposes of protein analysis. A state of the art miniature cutting tool may be delivered through a 23-gauge trocar. Needle aspiration may be performed with needles as small as 30-gauge (about half the diameter of 23 gauge). Fine gauge may increase the probability of a dry tap and/or change the properties of the aspirated material by acting as a filter. Small gauge may have an advantage in that traction may not be introduced on the gel matrix because the gel matrix cannot be pulled into the small needle bore. Vitreous samples are typically frozen or otherwise stabilized so that they can be processed in a laboratory outside of the operating room or ophthalmic office setting.

Injection of therapeutic doses of medication into the vitreous or aqueous humor inside the eye can increase IOP by as much as 25 mmHg, which is substantially greater than threshold levels that are considered potentially harmful. Evidence shows that while such TOP increases are transient, they are in fact associated with an iatrogenic glaucoma resulting in measurable loss of nerve fiber layer and visual function over a course of only several treatments in patients with 'normal' resting TOP. See Saxena, S., Lai, T. Y., Koizumi, H. et al., "Anterior chamber paracentesis during intravitreal injections in observational trials: effectiveness and safety and effects," *International Journal of Retina and Vitreous*, 5, 8 (2019). Therefore, it is sometimes desirable to remove a small volume of humor (whether aqueous, vitreous, or both) from the eye before injecting a comparable volume of medication. However, removal of a volume of humor may result in insufficient pressure, which can also be harmful to the eye. Therefore, in the case of diagnostic sampling of humors, it may be necessary or beneficial to inject a volume of fluid (whether medicated or otherwise) to replace the withdrawn humors. In either case, care must be taken to ensure that the removed and injected volumes are comparable, and in either case, two separate procedures (a sampling procedure and an injection procedure) are typically required.

It should therefore be appreciated that commonly used intravitreal injection and sampling methods have numerous drawbacks, including reduced and/or increased TOP and multiple needle sticks. Accordingly, there exists a need for improved intravitreal injection and sampling methods that address the forgoing and other concerns.

The information included in this Background section of the specification, including any references cited herein and any description or discussion thereof, is included for technical reference purposes only and is not to be regarded as subject matter by which the scope of the disclosure is to be bound.

SUMMARY

Disclosed is an intravitreal injection and sampling device that samples a quantity of vitreous or aqueous humor from the eye and injects a comparable volume of medicated or unmedicated injectant fluid to replace the sampled material, with a single needle stick and plunger press. The intravitreal injection and sampling device disclosed herein has particular, but not exclusive, utility for diagnosis and treatment of ophthalmic disorders of the human eye.

One aspect of the present disclosure includes an injection and extraction ophthalmic device that includes a housing configured to hold an injectant chamber configured to store an injectant, a plunger disposed within the injectant chamber, and a stopper coupled to a distal portion of the plunger. The device also includes a hypodermic needle disposed at a distal end of the housing, and a sample chamber located within the housing adjacent to the distal end. The housing, hypodermic needle, and sample chamber are arranged such that when the stopper is moved to a first depth within the housing, the sample chamber is configured to receive material via the hypodermic needle. The housing, hypodermic needle, and sample chamber are also arranged such that when the stopper is moved to a second depth within the housing exceeding the first depth, the injectant chamber is configured to dispense the injectant through the hypodermic needle.

Aspects of the present disclosure may also include one or more of the following features. The housing may be a double-barreled syringe, the injectant chamber may be disposed within a first barrel of the housing in fluid communication with the hypodermic needle, and the sample chamber may be disposed within a second barrel of the housing in fluid communication with the hypodermic needle. Moving the stopper to the first depth creates a volume of reduced pressure in the sample chamber, and moving the stopper to the second depth creates a volume of increased pressure within the injectant chamber.

In some aspects, the housing is a single-barreled housing, and the sample chamber is disposed within the housing between the injectant chamber and the distal end. A pressure difference within the sample chamber relative to an exterior pressure may be sufficient to draw material through the hypodermic needle into the sample chamber after the stopper is positioned at a first depth within the housing. The device may include a test, pre-loaded into the sample chamber or in fluid communication with the sample chamber, that provides a visual indication of a property of the sample of the material. The visual indication of the property of the material may inform a clinical decision about moving the stopper to the second depth. A volume of the injectant may be substantially equal to a volume of the material. A volume of the injectant or fluid sample may be in the range 0.01 milliliters (ml)-0.3 ml. The sample chamber may include a cooler or stabilizing chemical to stabilize the material for later analysis. The device may include a unique human-readable or machine-readable id associated with the device at time of manufacture. The device may include a portion on the device that can be tagged with an identifier unique to a patient. A distal tip of the hypodermic needle may configured to be extended or retracted in the material by a distance of between 1 millimeter (mm) and 6 mm during an interval between the drawing of the sample of the fluid into the sample chamber, and the dispensing of the injectant from the injectant chamber. The device may include a cutter incorporated onto the hypodermic needle. The sample chamber is configured to stop receiving the material when the injectant chamber is dispensing the injectant, and the injectant chamber is sealed from the injectant chamber when the sample chamber is receiving the material. The device is further configured so that no material is received into the sample chamber via the hypodermic needle and no injectant is dispensed from the injectant chamber through the hypodermic needle when the stopper is moved to a third depth within the housing greater than the first depth but less than the second depth. The device may include the injectant chamber; the plunger disposed within the injectant chamber; and the stopper coupled to the distal portion of the plunger.

One aspect of the present disclosure includes an injection and extraction ophthalmic device. The device includes a barrel comprising a chamber configured to contain a drug reservoir containing a liquid, and a plunger coupled to the drug reservoir. The device also includes a needle coupled to a distal end of the barrel, the needle comprising a proximal portion and a distal portion, the proximal portion extending proximally within the barrel, and the distal portion extending distally from the barrel. The device also includes a sample container positioned within the chamber of the barrel adjacent the proximal portion of the needle. The barrel, the needle, and sample container are configured such that when the plunger is moved to a first depth within the barrel, the needle is configured to enter the sample container; and when the plunger is moved to a second depth within the barrel exceeding the first depth, the drug reservoir is configured to dispense the liquid through the needle.

This Summary is provided to introduce a selection of concepts in a simplified form that are further described below in the Detailed Description. This Summary is not intended to identify key features or essential features of the claimed subject matter, nor is it intended to limit the scope of the claimed subject matter. A more extensive presentation of features, details, utilities, and advantages of the intravitreal injection and sampling device, as defined in the claims, is provided in the following written description of various embodiments of the disclosure and illustrated in the accompanying drawings.

BRIEF DESCRIPTION OF THE DRAWINGS

Illustrative embodiments of the present disclosure will be described with reference to the accompanying drawings, of which:

FIGS. 14A-14E illustrate the device of FIG. 13 in operation, in accordance with at least one embodiment of the present disclosure.

DETAILED DESCRIPTION

Figure 1:
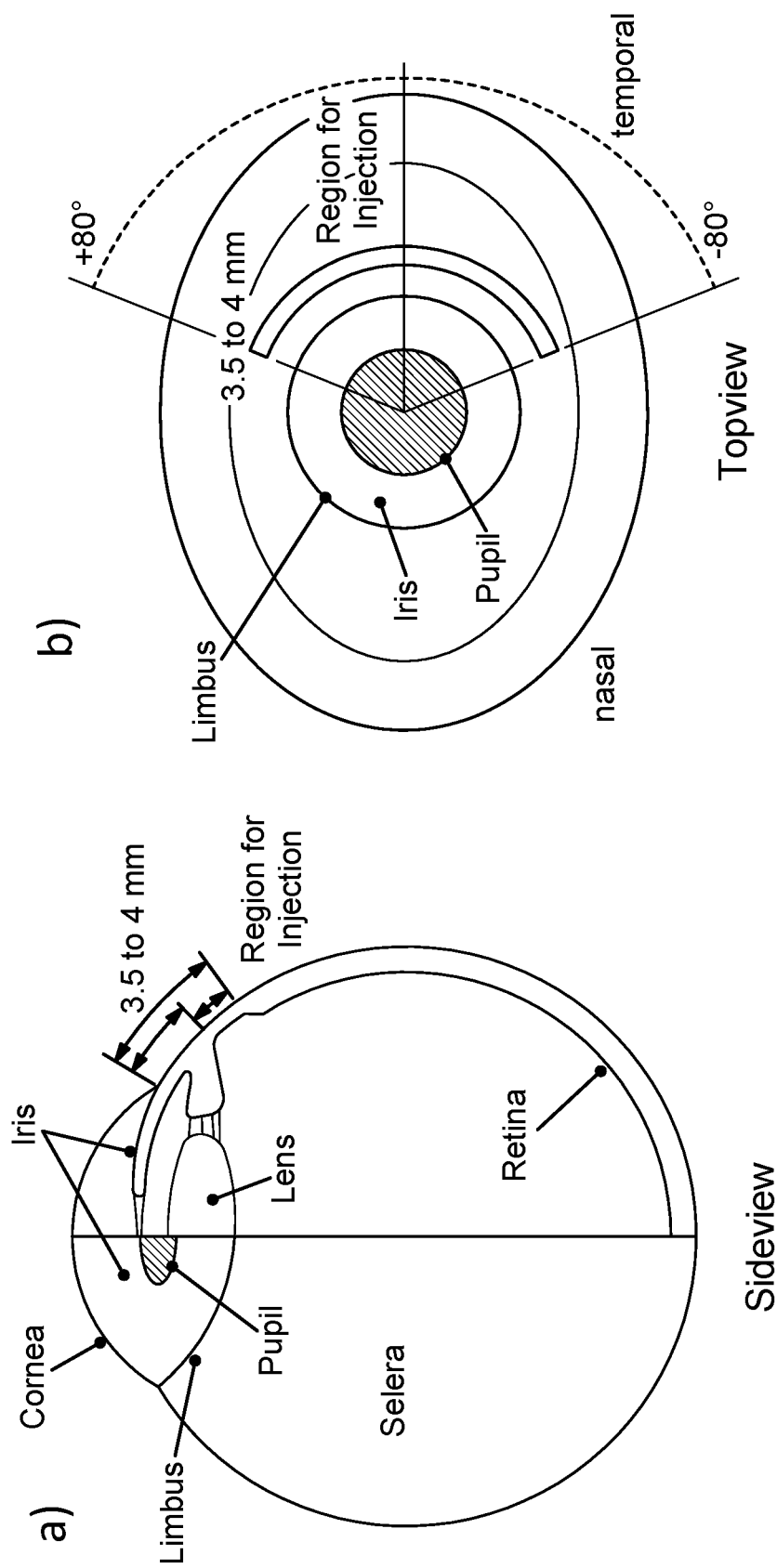
FIG. 1 is a diagrammatic representation of desirable needle insertion sites on the human eye, for intravitreal injection or sampling in accordance with at least one embodiment of the present disclosure.

In accordance with at least one embodiment of the present disclosure, an intravitreal injection and sampling device is provided which samples a quantity of vitreous or aqueous humor from the eye and injects a comparable volume of injectant fluid (medicated or unmedicated) to replace the sampled material, with a single needle stick and plunger press, requiring the same steps and motions as a standard injection procedure. The intravitreal injection and sampling device is a mechanical system that allows a physician to drive needle position relative to the conjunctiva in coordination with drive of plunger position, to actuate both sampling of, and injection into, the vitreous humor. In some embodiments, the device extracts between 50-300 microliters (μL) of vitreous humor prior to drug delivery in order to avoid an intraocular pressure (TOP) spike resulting from the injection. By withdrawing and injecting approximately equal volumes in a single procedure, the device enables the eye to maintain a relatively constant TOP.

In some embodiments, the device samples vitreous humor prior to injection. The intravitreal injection and sampling device may be a syringe that is supplied to the clinician prefilled with medicated fluid (e.g., anti-VEGF or steroid medication). A device for combined intravitreal injection, vitreous sampling, and sample handling is described, which permits acquisition of a vitreous sample and injection of a medicated fluid as a single procedure, without multiple insertions and separate needles required, as is currently the case. The device permits an unchanged physician workflow versus a standard needle injection and may enable a patient to get by with fewer visits and injections, with a lower chance of vision loss. In some embodiments, the device may include a retractable sheath that protects and hides the hypodermic needle before and after use. Immediate stabilization may be performed by chilling the entire syringe in a paired coolant canister, or by further drawing in of stabilizing fluid such as formalin into the syringe.

The extracted sample may be processed using a lateral flow assay, which is point-of-care compatible. Immediate processing may also take the form of pressing the sample back out onto a paper-based enzyme-linked immunoabsorbent assay (ELISA) test to give a color-based indicator of the amount of a particular analyte present, where the analyte measured is tailored to the type of drug injected. For example, injection of an anti-VEGF medication may be paired with a pressure-mediated ELISA (pELISA) indicating a threshold amount of VEGF present in the vitreous. A broad-spectrum, first-line antibiotic may be paired with a test indicating the presence of bacteria of different types to guide follow up with a more specific treatment. Anti-inflammatories may be paired with tests indicating the types of immune cells or immune mediator proteins. Other methods, such as well-based ELISA or pressure mediated ELISA may be utilized to analyze the extracted sample. In some embodiments, the sample may be withdrawn before the injection is delivered. A larger-gauge needle including a cutter to liquefy the vitreous can minimize the potential for a dry tap, as well as minimize the potential that traction is created when the vitreous gel is drawn into the needle. Vitrectomy devices typically pull the vitreous by suction into a port at the side of the needle where a rapidly moving blade cuts the gel into manageable pieces. Two sharp edges may come together in a scissors like motion to cut the gel. In this case, one of the edges is provided by the static edge of the port on the side of the trocar, and an internal blade may move in a rotary or piston-like motion relative to the sharp edges of the port. In some examples, the internal blade is obviated by high frequency ultrasound vibrations that oscillate the tip of the needle such that the edges of the port itself cut through the vitreous humor. In this embodiment, an external power source is magnetically coupled to the cutter to sterilely drive its motion. Liquified vitreous gel is drawn into a holding chamber by the forward motion of a primary plunger and the suction created on the back side of the primary plunger. A Peltier junction, gas expansion cooler, chemical reaction cooler, or other cooling device attached to the holding chamber may rapidly freeze the vitreous sample for laboratory post processing. During this time the front side of the primary plunger may be pushing against air, which may be released via an escape. When a sample volume substantially equal to volume of drug to be delivered has been withdrawn, the primary plunger contacts a secondary plunger that pushes the drug into the eye. The cutter blade stops liquefying the vitreous humor as the drug begins to push around the cutter drive shaft into the region of the vitreous that has been previously sampled. The cutter drive shaft is optimized to create a very low dead volume in the needle bore. Labeling on the device may uniquely identify the sample to the laboratory, in a way that laboratory results can be easily attached to the patient record of interest.

The present disclosure aids substantially in intraocular injection and sampling with a single handheld device operated by a single needle stick and the depression of a single plunger. This streamlined sampling and injection procedure transforms a demanding multi-step process into a single motion, comparable to delivering an injection, without the normally routine need to perform a separate sampling step before or after the injection, or a separate injection step before or after the sampling. This unconventional approach improves the functioning of the intravitreal injection or sampling device, by permitting both injection and sampling to be performed with a single needle stick and plunger press.

Intravitreal injection is typically delivered by an ophthalmologist but has been successfully performed by physician extender personnel with an adequate certification program. The present disclosure may serve to reduce the amount of training required to perform an injection or sampling procedure.

These descriptions are provided for exemplary purposes only and should not be considered to limit the scope of the intravitreal injection and sampling device. Certain features may be added, removed, or modified without departing from the spirit of the claimed subject matter.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. The examples described below are provided for purposes of illustration and are not intended to be limiting.

FIG. 1 is diagrammatic representation of exemplary desirable needle insertion sites on the human eye, for intravitreal injection or sampling in accordance with at least one embodiment of the present disclosure. For sampling of and injection into the vitreous humour, desirable needle insertion sides may occur for example in a narrow region about 3.5 to 4.0 mm outside the limbus (outer edge of the iris), on the temporal side of the eye, within an arc of ±80° from the eye's horizontal axis.

Figure 2:
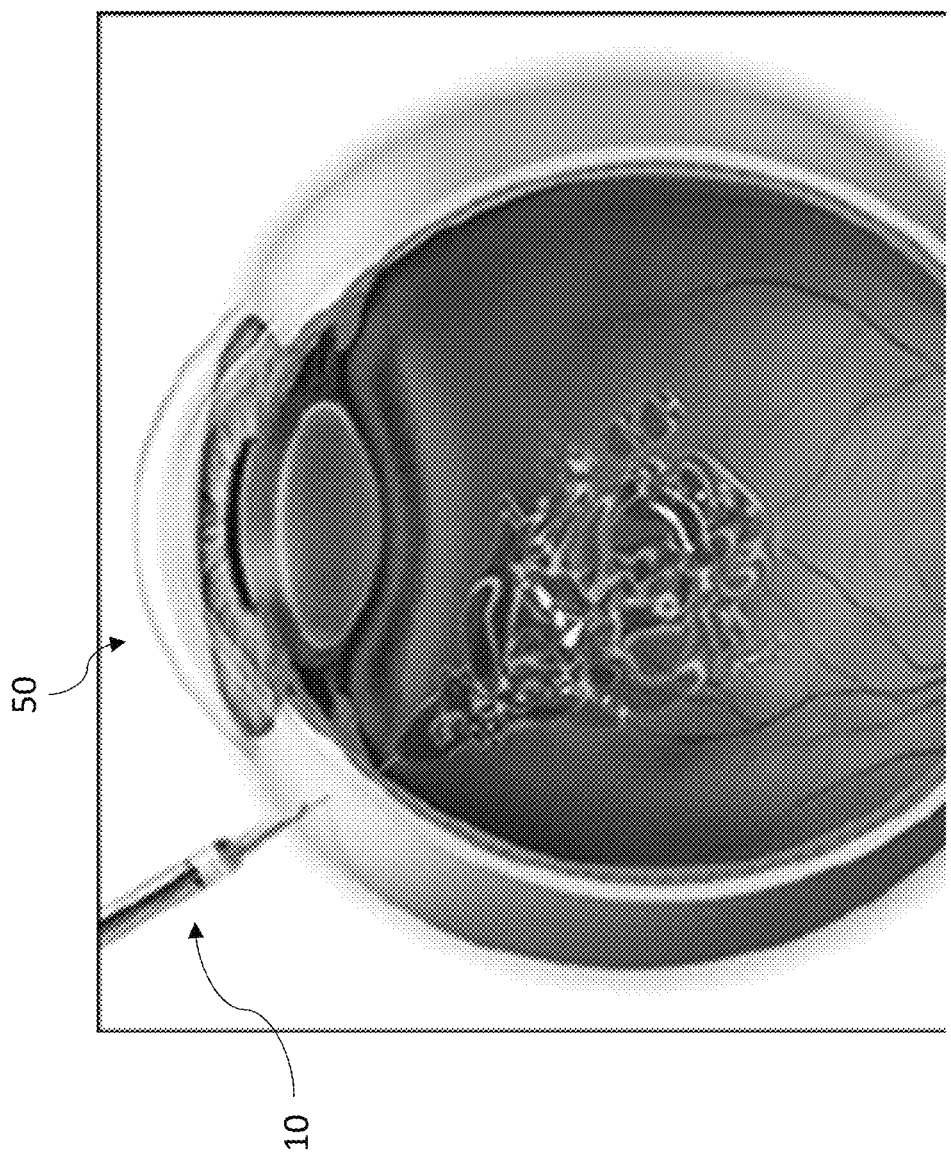
FIG. 2 is a side cross-sectional view of a hypodermic needle injecting a fluid into a human eye, in accordance with at least one embodiment of the present disclosure.

FIG. 2 is a side cross-sectional view of a hypodermic needle 10 injecting a fluid into a human eye 50, in accordance with at least one embodiment of the present disclosure. Intravitreal injection may occur for example with a needle insertion roughly perpendicular to the surface of the eye at the insertion site and may increase intraocular pressure (TOP) by as much as 25 mmHg if a comparable volume of material is not removed from the eye before, during, or after the injection.

Figure 3:
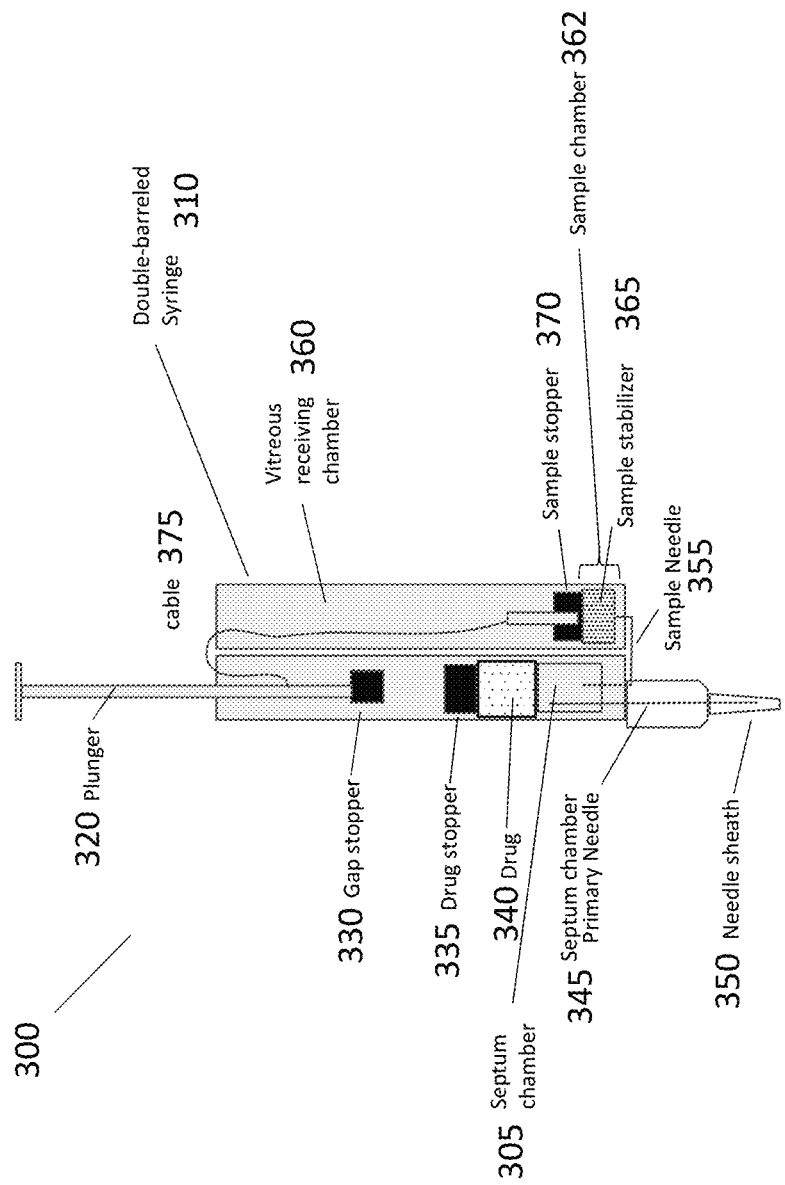
FIG. 3 is a diagrammatic, cross-sectional side view of an exemplary intravitreal injection and sampling device, in accordance with at least one embodiment of the present disclosure.

FIG. 3 is a diagrammatic, cross-sectional side view of an exemplary intravitreal injection and extraction, or sampling, ophthalmic device 300, in accordance with at least one embodiment of the present disclosure. The exemplary device includes a cable guide in a double-barreled syringe 310 or other housing, for drug delivery coordination with sample extraction, and uses a semi-stable connection to achieve release at a predefined stroke length. Visible are a septum chamber 305, plunger 320, gas stopper 330, drug stopper 335, drug chamber 340, septum chamber needle or primary hypodermic needle 345, needle sheath 350, sample hypodermic needle 355, vitreous receiving barrel 360, sample stabilizer 365, sample stopper 370, and cable 375. The primary needle 345 may for example be a 30 G sideport canula, although other types of needles may be used instead or in addition.

In an example a clinician prepares a sterile field as with standard delivery (e.g., iodine on the surface of the eye, with an optional speculum to hold the eyelids open). The clinician then presses the needle sheath 350 against the surface of the eye at a desirable injection side (e.g., 4 mm temporal from the limbus, or outer edge of the iris), and inserts the needle (e.g., to a depth of about 6 mm). The clinician then depresses the plunger 320 until the top of the primary needle 345 is nearly in contact with the top surface of the septum chamber (e.g., nearly in contact with the drug). Depression of the plunger pulls downward on the cable 375, which (due to cable action) pulls the sample stopper upward, increasing the volume of an extraction or sample chamber 362 within the vitreous receiving barrel 360 as the sample stopper 370 is moved in a direction within the receiving barrel 360 away from the sample needle 355, thereby creating a negative pressure within the sample chamber 362. Vitreous humor is then drawn upward through the primary needle 345, laterally through the septum chamber 305 to the sample needle 355, and into the sample chamber 362 within the vitreous receiving barrel 360.

The clinician then waits (e.g., for about 2 seconds) for the sample chamber volume to fill, and then depresses the plunger 320 to full depth. This causes the upper end of the primary needle 345 to penetrate the top surface of the septum chamber 305 and come in contact with the drug chamber 340, thereby ceasing the withdrawal of vitreous humor from the eye through the primary needle 345. The drug container 340 is then injected downward into the eye through the primary needle 345 through the action of the plunger 320. In some aspects, the drug chamber 340 may be configured to contain and dispense a volume of material equal to or approximately equal to the volume of material obtained and stored in the sample chamber 362. In some aspects, the drug chamber 340 is configured to contain, and the sample chamber 362 is configured to receive volumes of a liquid ranging from 0.01 milliliters (mL)-0.3 mL, including values such as 50 uL, 100 uL, 150 uL, and 200 uL. The clinician then removes the needle 345 from the eye and provides post-injection care as typical (e.g., medicated Q-tip on injection site). The needle sheath 350 automatically protects the needle 345 as it is withdrawn. The clinician then sets the intravitreal sampling and injection device 300 aside for sample handling by staff members (instead of disposal in a sharps container). In an example, the intravitreal injection and sampling device 300 withdraws a volume of vitreous humor into the vitreous receiving chamber that is comparable to the volume of drug injected, thus permitting the eye to maintain normal TOP.

In some embodiments, point of care testing may be built into the device. For example, a lateral flow assay such as a VEGF threshold indicator material may be embedded in the vitreous receiving chamber, such that the indicator material will change color if VEGF is present in the sample above a threshold concentration, or in proportion to the VEGF concentration. In some cases, the results of these tests may inform the decision as to whether to continue to depress the plunger and thus inject the drug. Alternatively, a similar test may be included in an accompanying kit such that the extracted vitreous humor is expelled onto the test apparatus after extraction. This may enable multiple tests to be performed on the same sample.

Figure 4:
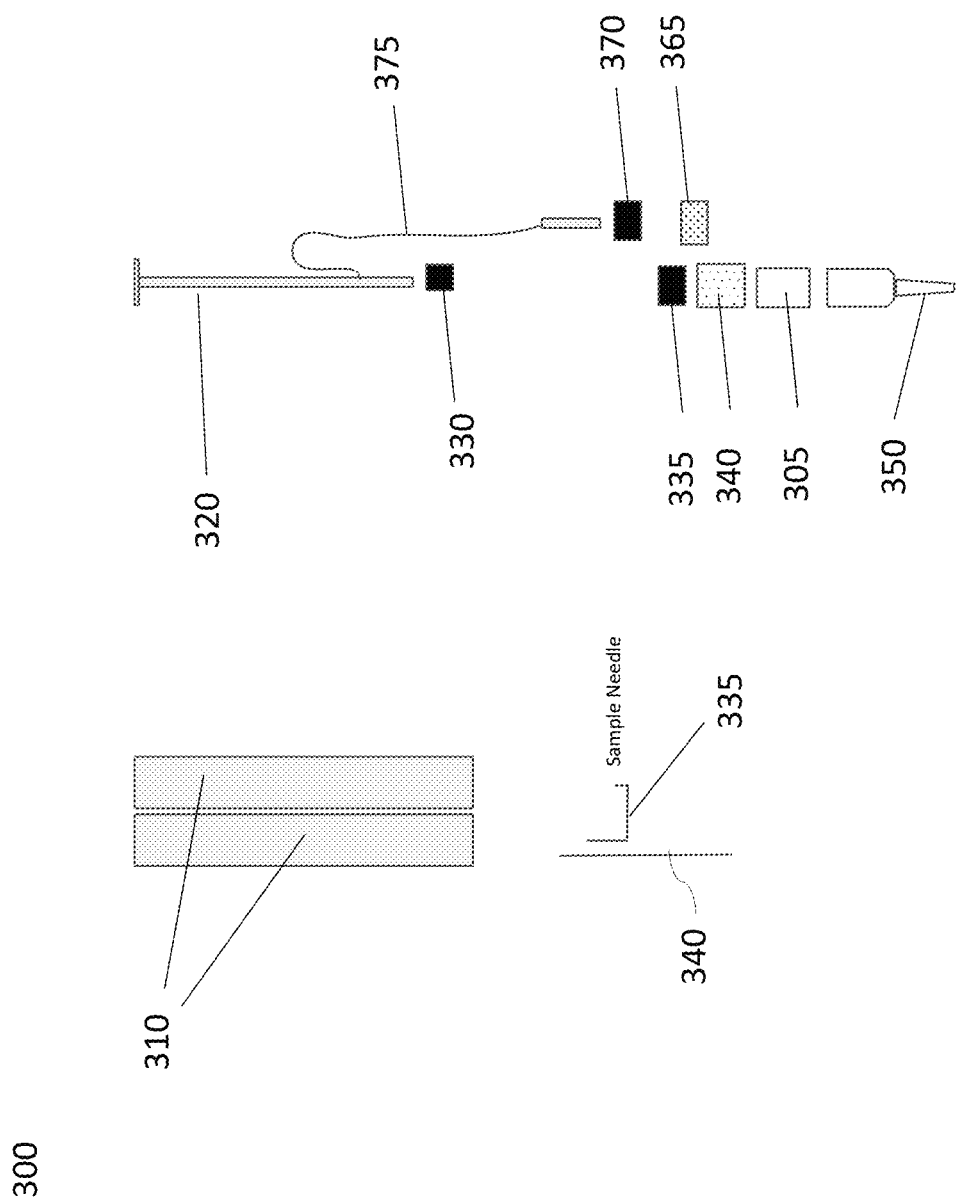
FIG. 4 is a disassembled view of the components of an exemplary intravitreal injection and sampling device, in accordance with at least one embodiment of the present disclosure.

FIG. 4 is a disassembled view of the exemplary intravitreal injection and sampling device 300 illustrated in FIG. 3, in accordance with at least one embodiment of the present disclosure. Visible in FIG. 4 are the double-barreled syringe 310, primary needle 345, and sample needle 355. Also Visible in FIG. 4 are the plunger 320, cable 375, gas stopper 330, drug stopper 335, drug container 340, septum chamber 305, needle sheath 350, sample stopper 370, and sample stabilizer 365. In some embodiments, the device also includes semi-stable cable end connections (e.g., using narrow slice in molded thermoplastic), and the interconnected multi-barrel syringe may for example be of molded plastic. The sample acquisition mechanism is as described above for FIG. 3.

Figure 5:
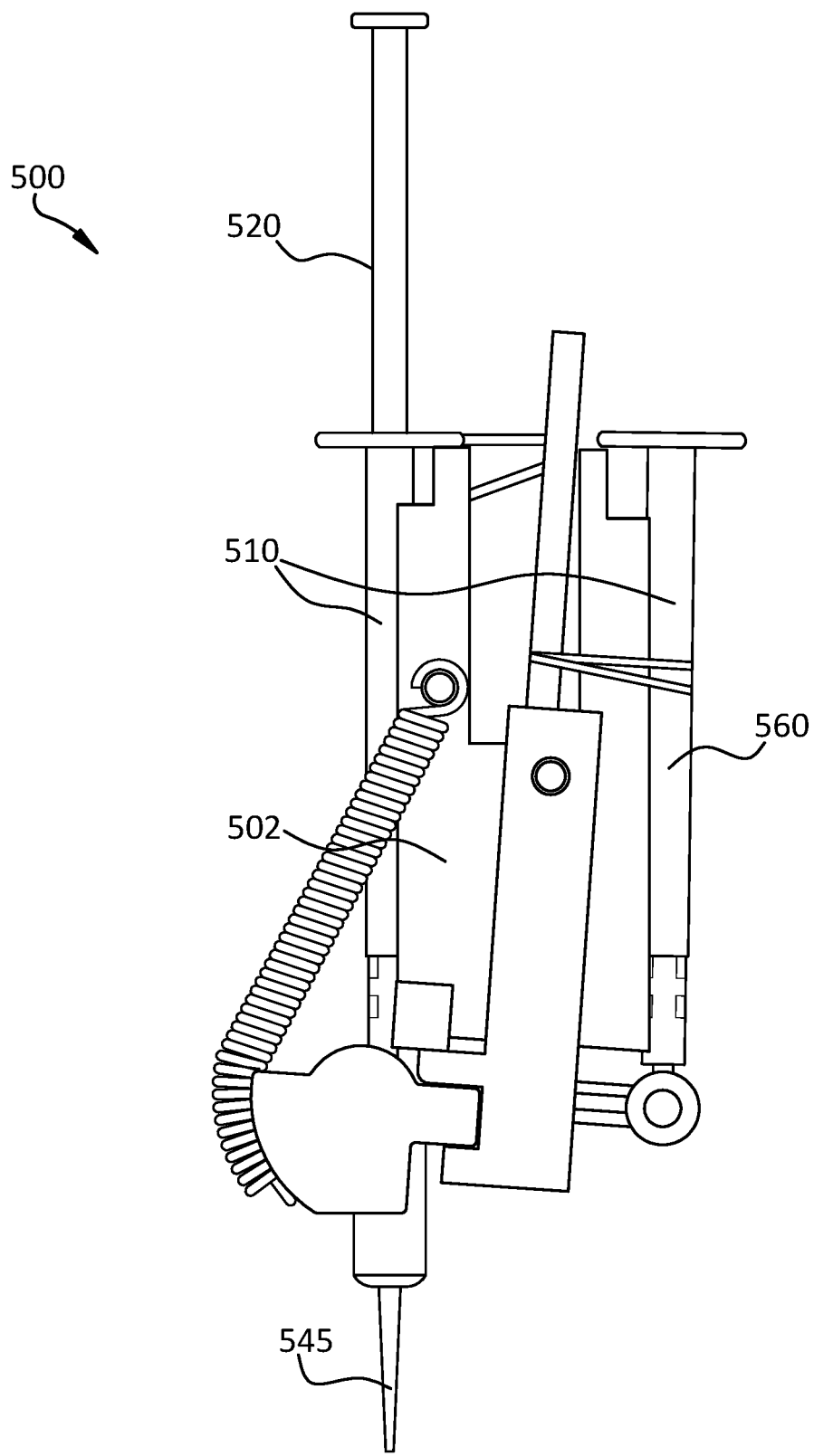
FIG. 5 is a side view of an assembled exemplary intravitreal injection and sampling device, in accordance with at least one embodiment of the present disclosure.

FIG. 5 is a side view of an assembled exemplary intravitreal injection and sampling device 500, in accordance with at least one embodiment of the present disclosure. Visible are the plunger 520, double-barreled syringe 510, primary needle 545, and molded plastic structural components 502. The exemplary device 505 uses a cable system, on depression of the plunger 520, to first draw up fluid through a sampling syringe 560, similar to the device 300 shown in FIGS. 3 and 4. After hitting full draw, a portion of the drawing plunger 520 separates and triggers release on a spring to change a direction of a valve, closing the sampling side and opening the injection side, then the plunger handle contacts a silicone plunger element to actually pushes medication out through the syringe.

Figure 6:
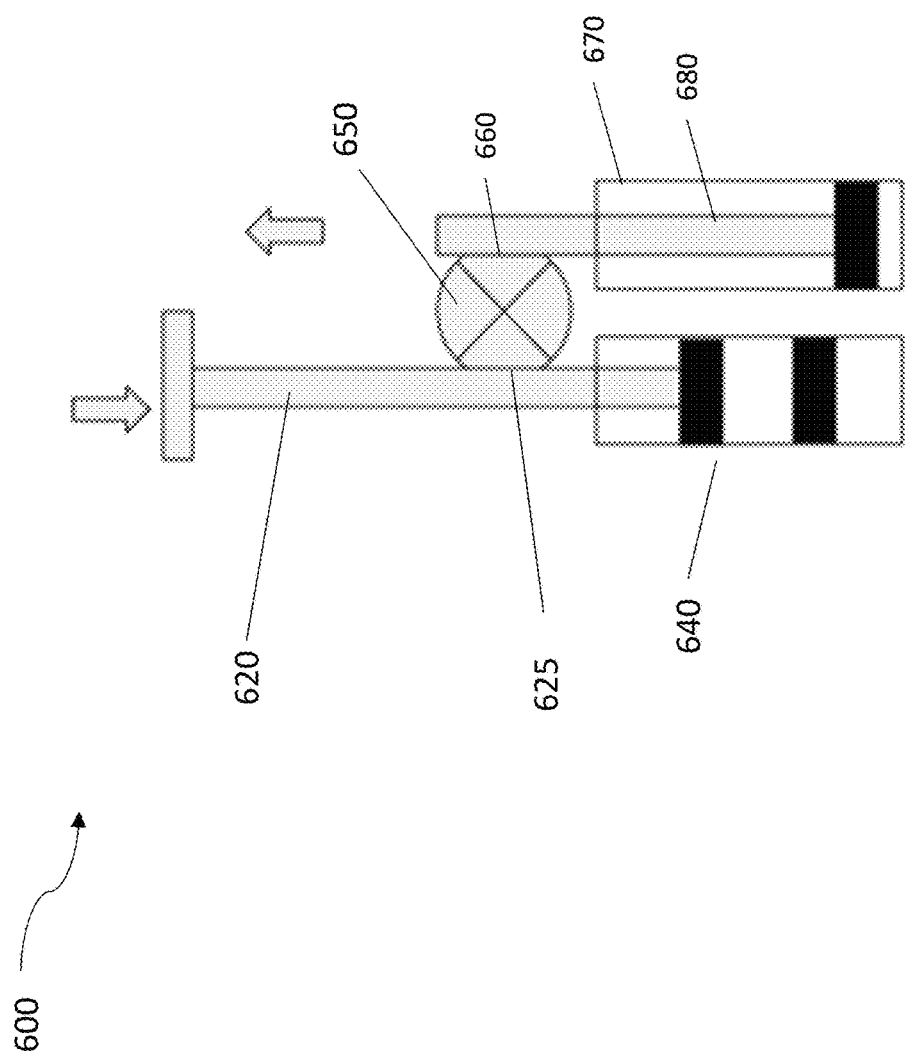
FIG. 6 is a diagrammatic, cross-sectional side view of an alternative actuation mechanism for an exemplary intravitreal injection and sampling device, in accordance with at least one embodiment of the present disclosure.

FIG. 6 is a diagrammatic, cross-sectional side view of an alternative actuation mechanism for an exemplary intravitreal injection and sampling device 600, in accordance with at least one embodiment of the present disclosure. In this example, a rack and pinion system coordinates simultaneous or subsequent sampling and drug delivery through two syringes 640, 670. The rack and pinion system may include placement of teeth to achieve predefined stroke lengths between the two syringes that may be equal or unequal depending on the implementation. Changing the position of the teeth on the two racks easily allows for limited travel of sample plunger relative to the motion of the plunger. The device 600 includes a first rack 625 for actuating the drug injection portion of the device 600, and a second rack 660 for actuating the sampling portion of the device 600. The racks 625, 660 cooperate with the pinion 650 to cause the opposing motions of the first plunger 620 for drug injection, and a second plunger 680 for creating a negative pressure to draw a sample from the eye. Each syringe 640, 670 may be coupled to a corresponding needle such that the drug is injected through a first needle while the sample is drawn through the second needle.

Figure 7B:
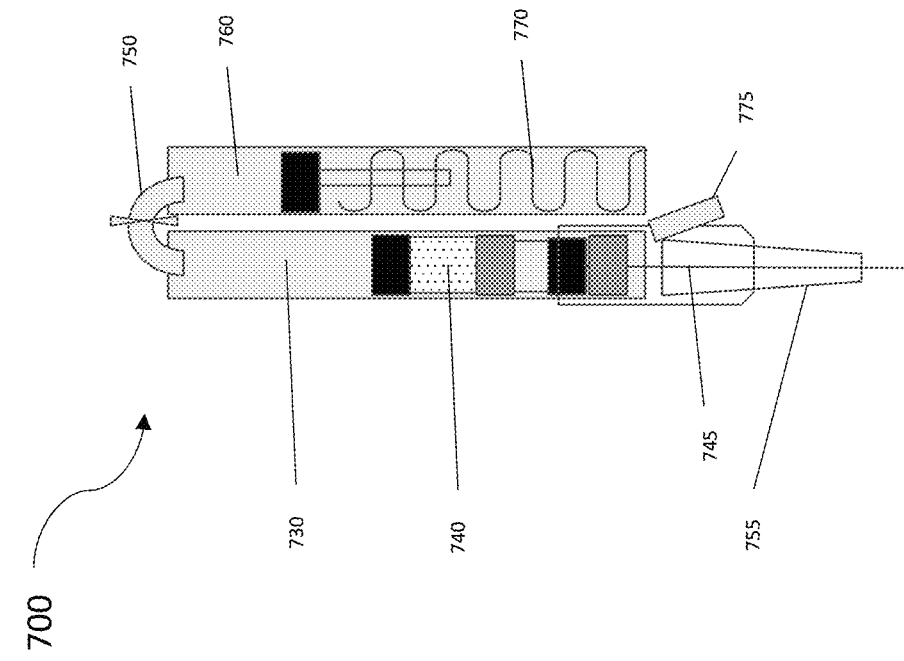
FIGS. 7A-7B are diagrammatic, cross-sectional views of an alternative actuation mechanism for an exemplary intravitreal injection and sampling device, in accordance with at least one embodiment of the present disclosure.
Figure 7A:
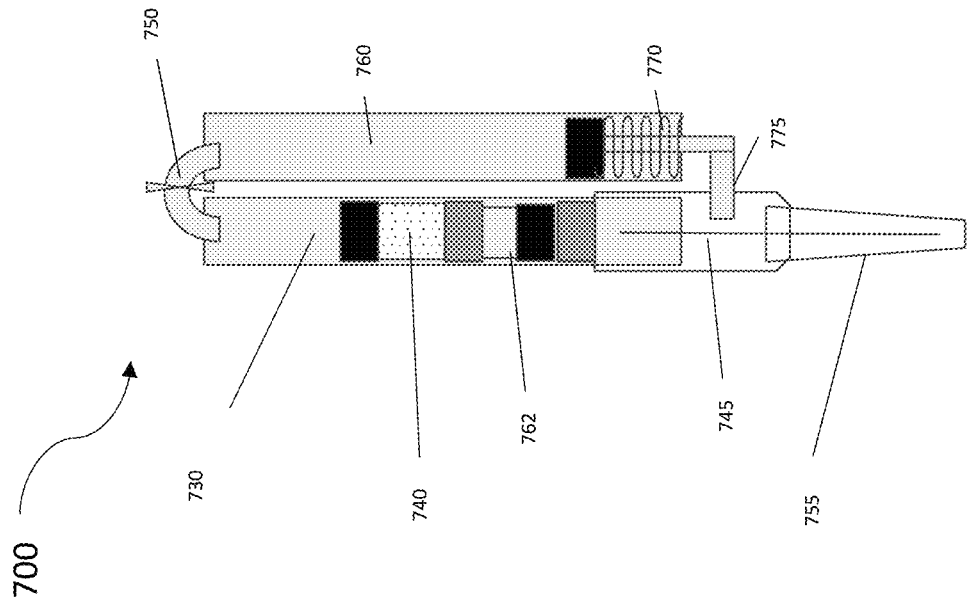

FIGS. 7A-7B are diagrammatic, cross-sectional views of an alternative actuation mechanism for an exemplary intravitreal injection and sampling device 700, in accordance with at least one embodiment of the present disclosure. In this example, an injection-depth-sensing, triggered actuation mechanism includes a spring-driven hydraulic actuator, including a hydraulic chamber 760 containing a hydraulic fluid beside a vacuum stoppered cartridge 730. A flow restriction 750 (e.g., a Venturi) permits the hydraulic fluid to push at a desired rate, to give a predefined time for sampling, and a sufficient drug ejection rate to guarantee captured vitreous forced release. A trigger 775 is arranged to cooperate with a retracting sheath 755, which is configured to actuate the trigger 775 to release an energy storage device 770, which includes a pre-loaded spring. The sheath 755 is configured such that, when the needle 745 protrudes out a distal opening of the sheath 755 and into the eye by a certain amount (e.g., 5-10 mm), the proximal end of the sheath 755 causes the trigger 775 to release or actuate. With the release of the energy storage device 770 by the depth-sensing trigger 775, the hydraulic fluid 760 pushes the contents of the device 700 through the syringe body 730 toward the needle 745, such that the needle 745 successively punctures one or more septa or seals to advance into the evacuated sample chamber 762 for a first period of time, and then into the drug container 740 for a second amount of time. The energy storage device 770 may store sufficient energy (e.g., compressed spring energy, compressed gas) to push the chambers 740, 762, and their corresponding septa, to a distal stopping point, as shown in FIG. 7B. In some aspects, the evacuated sample chamber 762 comprises a sealed container configured to maintain a negative air pressure or fluid pressure relative to the external environment (e.g., air, pressure of the vitreous chamber).

Figure 8:
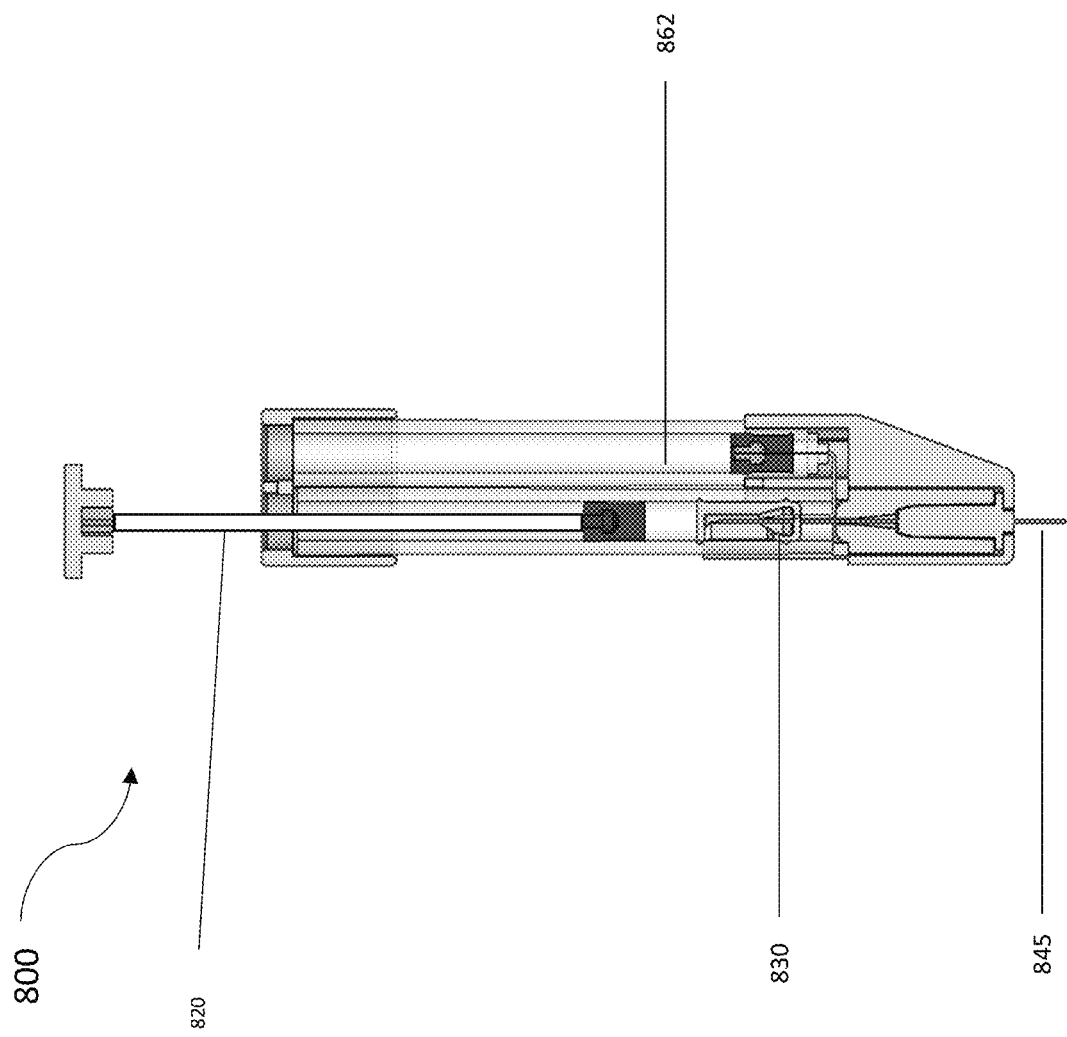
FIG. 8 is a diagrammatic, cross-sectional view of an alternative actuation mechanism for an exemplary intravitreal injection and sampling device, in accordance with at least one embodiment of the present disclosure.

FIG. 8 is a diagrammatic, cross-sectional view of an alternative actuation mechanism for an exemplary intravitreal injection and sampling device 800, in accordance with at least one embodiment of the present disclosure. In this example, an air hydraulic design includes a precise seal around the plunger shaft 820, and valves to ensure the drug flows only outward through the needle 845, and the sampled vitreous humor flows only inward into the sample chamber 862.

A valve 830 starts in a sampling position prior to needle insertion. When the needle 845 is inserted to full depth in the eye, the valve 830 allows vitreous humor to be pulled into the device. After a time delay (after which a sufficient sample of vitreous humor should be pulled up if the sample draw is not a dry tap), the valve 830 moves to next position, where it is ready to push the injection. Again, an outer protective cap prevents the needle from being exposed as a risk, and the portion touching eye may provide a disinfectant swab.

Figure 9:
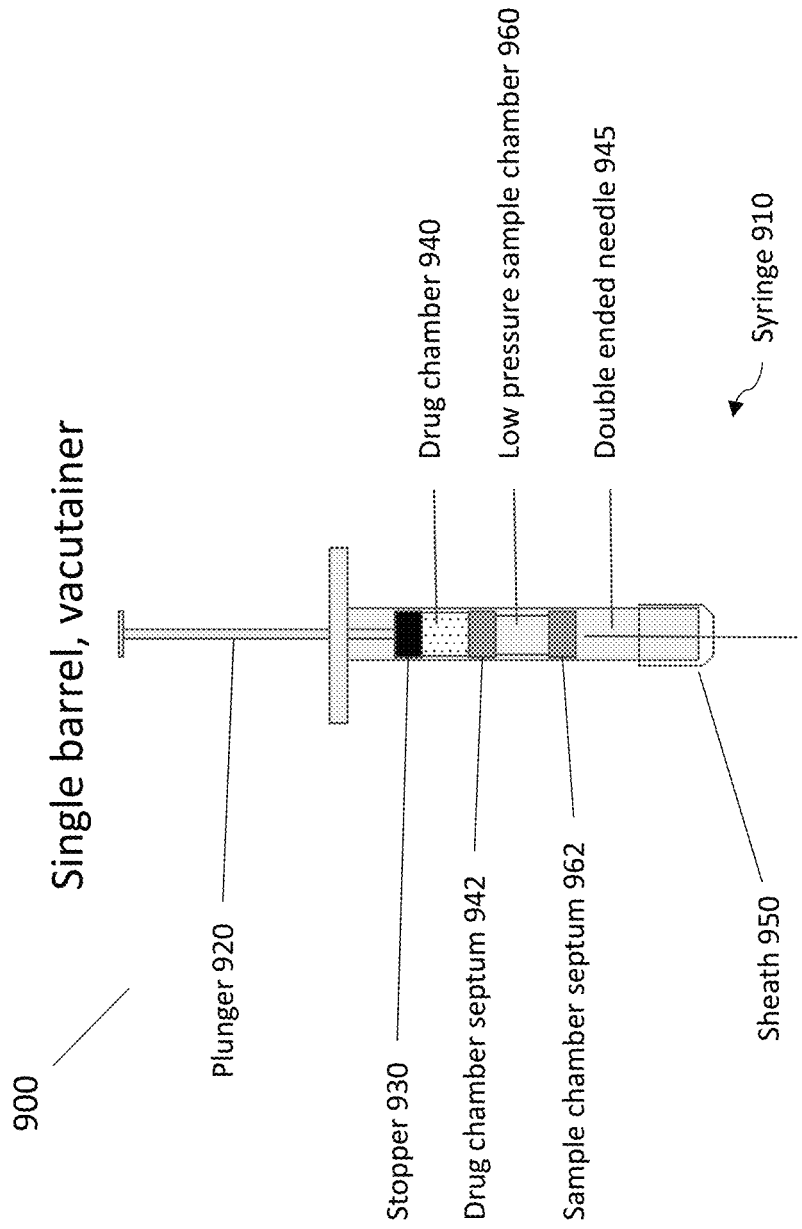
FIG. 9 is a diagrammatic, cross-sectional side view of an exemplary simplified embodiment of an intravitreal injection and sampling device, in accordance with at least one embodiment of the present disclosure.

FIG. 9 is a diagrammatic, cross-sectional side view of an exemplary simplified embodiment of an intravitreal injection and extraction, or sampling, device 900, in accordance with at least one embodiment of the present disclosure. Visible are the syringe 910, plunger 920, stopper 930, drug chamber 940, drug chamber septum 942, low-pressure sample chamber 960, sample chamber septum 962, double-ended needle 945, and sheath 950. In some aspects, the drug chamber 940 may be referred to as a drug reservoir, which is configured to contain and dispense a liquid. The illustrated example uses a pre-vacuum-loaded sample chamber 960 (potentially containing various proteomic tests, without the space constraints of previous embodiments). In an example, the septa 942, 962 are floating within the syringe 910, rather than attached, and are made of an injection-molded soft sealing material. Alternatively, the septa 942, 962 can be made of a rigid, thin, pierceable material sealed against the syringe 910 with o-rings. In an example, the low-pressure sample chamber 960 has a volume of 50-300 uL, formed in the syringe 910 as part of the stoppering process. In an example, the low-pressure sample chamber 960 may be a type or form of vacutainer.

In this example, when the needle 945 is inserted into the eye and the plunger 920 is depressed, the top end of the double-ended needle 945 pierces the sample chamber septum 962. Low pressure in the sample chamber 960 then causes vitreous humor to be drawn upward through the needle into the sample chamber. As the sample chamber 960 fills with sampled vitreous humor, continued depression of the plunger 920 brings the top end of the needle 945 into contact with the drug chamber septum 942 (ideally, at the same moment that the sample chamber is filled to a desired level). When the needle 945 pierces the drug chamber septum 942, sampling of the vitreous humor ceases, and the end of the needle 945 is now in fluid communication with the drug chamber 940, such that further depression of the plunger 920 causes the drug to be injected into the eye. When the plunger 920 is fully depressed, the full dose of drug has been injected into the eye. At this point, the needle 945 is withdrawn from the eye, and post-injection care and sample handling/analysis operations may commence.

In some embodiments, the drug chamber 940 may be replaced with a second low-pressure sample chamber (e.g., one with different testing/indicating materials coated onto its walls).

Figure 10:
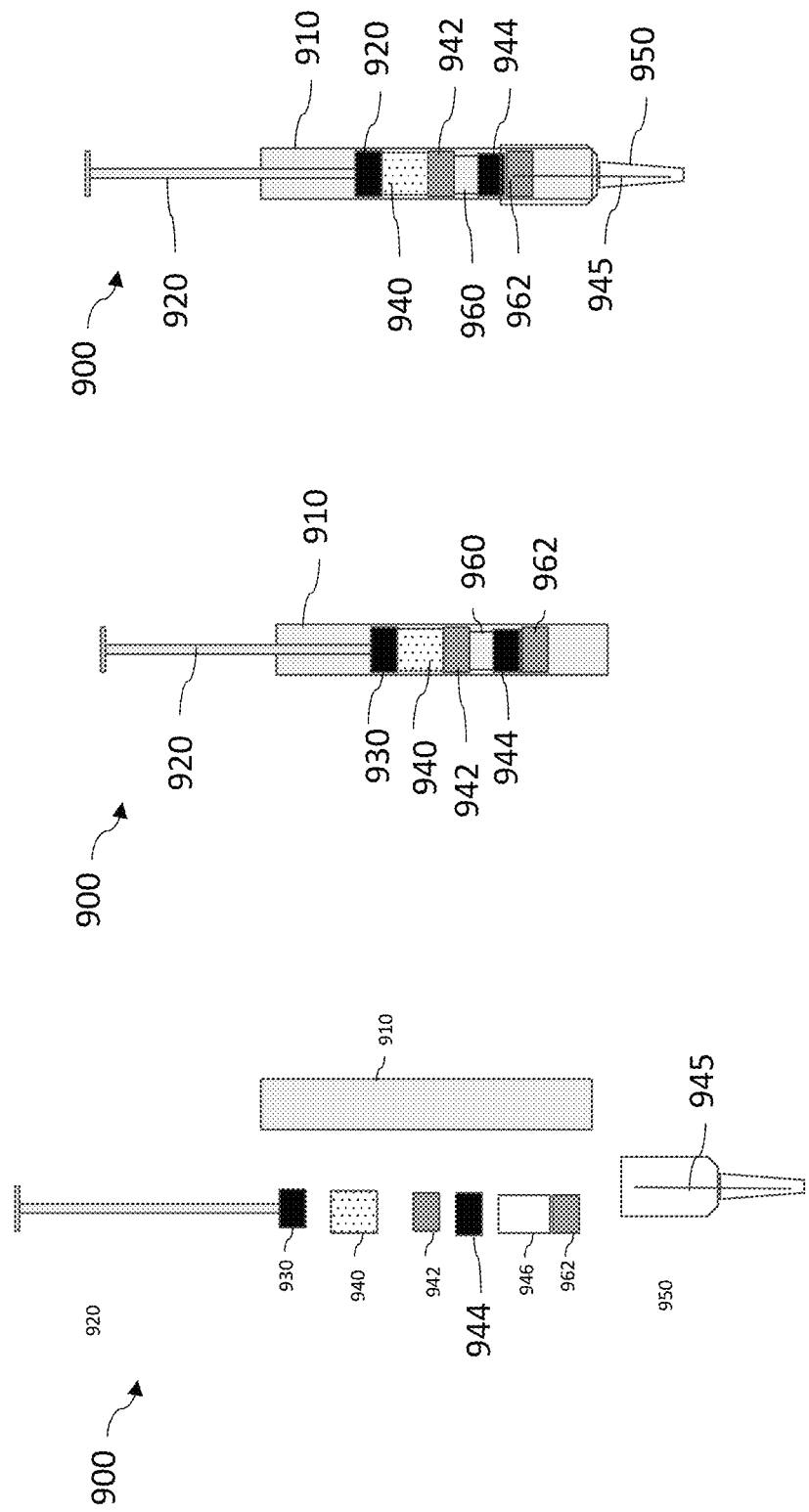
FIG. 10A-10C are diagrammatic, cross-sectional side views of the components of the embodiment shown in FIG. 9.

FIGS. 10A-10C are cross-sectional side views of the components of the device 900 of FIG. 9, shown at various stages during assembly and/or use. Visible are a plunger 920, drug stopper 930, drug chamber 940, internal septa or drug chamber septa 942, sample stabilizer 944, chamber spacer 946 that forms the sample chamber, external septa or sample septa 962, gas-impermeable syringe tube 910, needle 945, and sheath 950. In FIG. 10B, which is associated with a first portion of an assembly and usage process, all of these components except the needle 945 and sheath 950 are assembled as shown, using a vacuum stoppering process that creates a vacutainer or low-pressure sample chamber 960 and a separate drug-filled drug chamber 940. In FIG. 10C, which is associated with a second portion of the assembly and usage process, the needle 945 and sheath 950 are attached, thus creating a finished intravitreal injection and sampling device 900.

In some aspects, an intravitreal injection and sampling device may be inserted into a vitreous humor of an eye, and may be inserted to a depth of about 6 mm in the eye. The injection and sampling device may include one or more of the devices 300, 500, 600, 700, 800, 900 described above, for example. Accordingly, the device may include a sample container configured to store a vacuum (e.g., evacuated container), or a chamber having a vacuum mechanism, such as a plunger configured to create a negative plunger within the chamber, for example. The device may draw a sample of the vitreous humor simulant of the simulated eye, in accordance with at least one embodiment of the present disclosure. In an example, the plunger is depressed until the top end of the needle pierces the sample chamber septum, causing vitreous humor simulant to be pulled through the needle into the sample chamber. The sample chamber is then filled to a desired level with vitreous humor simulant (red), and then continued depression of the plunger has caused the top end of the needle to pierce the drug chamber septum, causing the drug (blue) to be injected downward through the needle into the vitreous humor of the simulated eye.

When the plunger of the device is fully depressed, a full dose of drug simulant is injected into the simulated eye. In an example, if the clinician operating the intravitreal injection and sampling device depresses the plunger over a long enough period of time (e.g., four or more seconds), the sample chamber can be filled to a desired level and a full dose of the drug can be dispensed into the eye with a single, smooth depressive motion, with no need to pause while the sample chamber fills.

Figure 11:
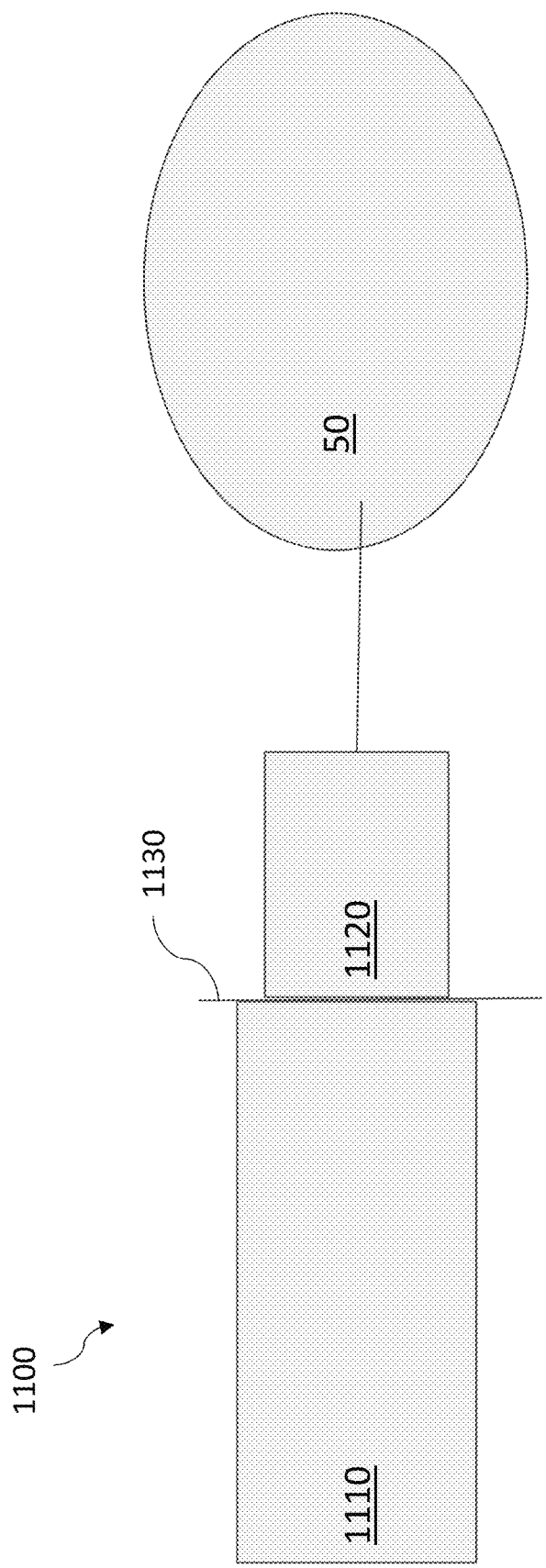
FIG. 11 is a diagrammatic side view of an alternative embodiment of the intravitreal injection and sampling device, wherein the sample chamber is in gaseous communication with a larger low-pressure chamber, in accordance with at least one embodiment of the present disclosure.

FIG. 11 is a diagrammatic side view of an alternative embodiment of an intravitreal injection and sampling device 1100, wherein the sample chamber 1120 is in gaseous communication with a larger low-pressure chamber 1110, in accordance with at least one embodiment of the present disclosure. This device 1100 includes a gas-permeable filter 1130 (whether rigid or flexible) that maintains a separate chamber from the sample chamber 1120 and can be evacuated independently. This permits the volume of vacuum to be larger than the volume of the sample chamber, thus ensuring that the sample chamber is able to fill completely with vitreous humor, without the risk of accidentally pulling too much material from the eye. A material such as Gore-Tex may be used for the spacer. In some examples, force measurement on barrier might be used to trigger mechanism to recognize that the desired sample volume has been achieved. Any additional evacuated volume is not subject to sample filling.

Figure 12:
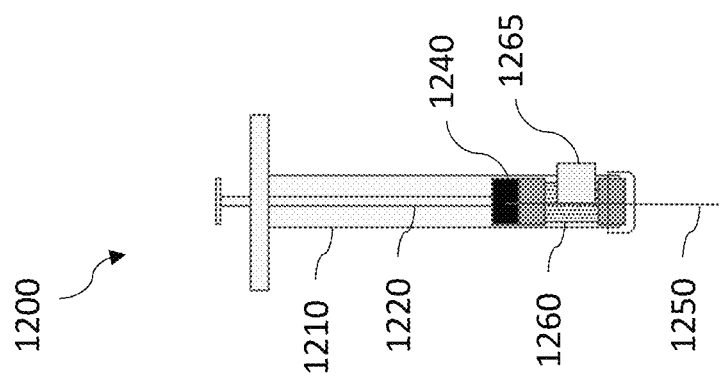
FIG. 12 is a diagrammatic side view of an alternative embodiment of the intravitreal injection and sampling device, wherein the sample chamber is configured for removal of the sample material, in accordance with at least one embodiment of the present disclosure.

FIG. 12 is a diagrammatic side view of an alternative embodiment of an intravitreal injection and sampling device 1200, wherein the sample chamber 1260 is configured for removal of the sample material, in accordance with at least one embodiment of the present disclosure. The device 1200 includes a syringe body 1210, a plunger 1220 having a stopper 1240 at a distal end of the plunger 1220, and a sample chamber 1260 having septa or seals at a distal and proximal end of the sample chamber 1260. In some aspects, the distal septa may be pierceable by a proximal end of the needle 1250 to allow the sample to flow into the evacuated space of the sample chamber 1260. For embodiments where testing materials are not coated on the walls of the sample chamber 1260, and/or where it is desired to perform other tests or additional tests, the syringe body may contain a frangible portion 1265 such that it can be broken to allow controlled access to the sample without contaminating it. Alternatively, features may be included in the syringe body 1210 to facilitate drilling or piercing to withdraw the sample. This may permit the same sample to be employed in multiple different tests.

Figure 13:
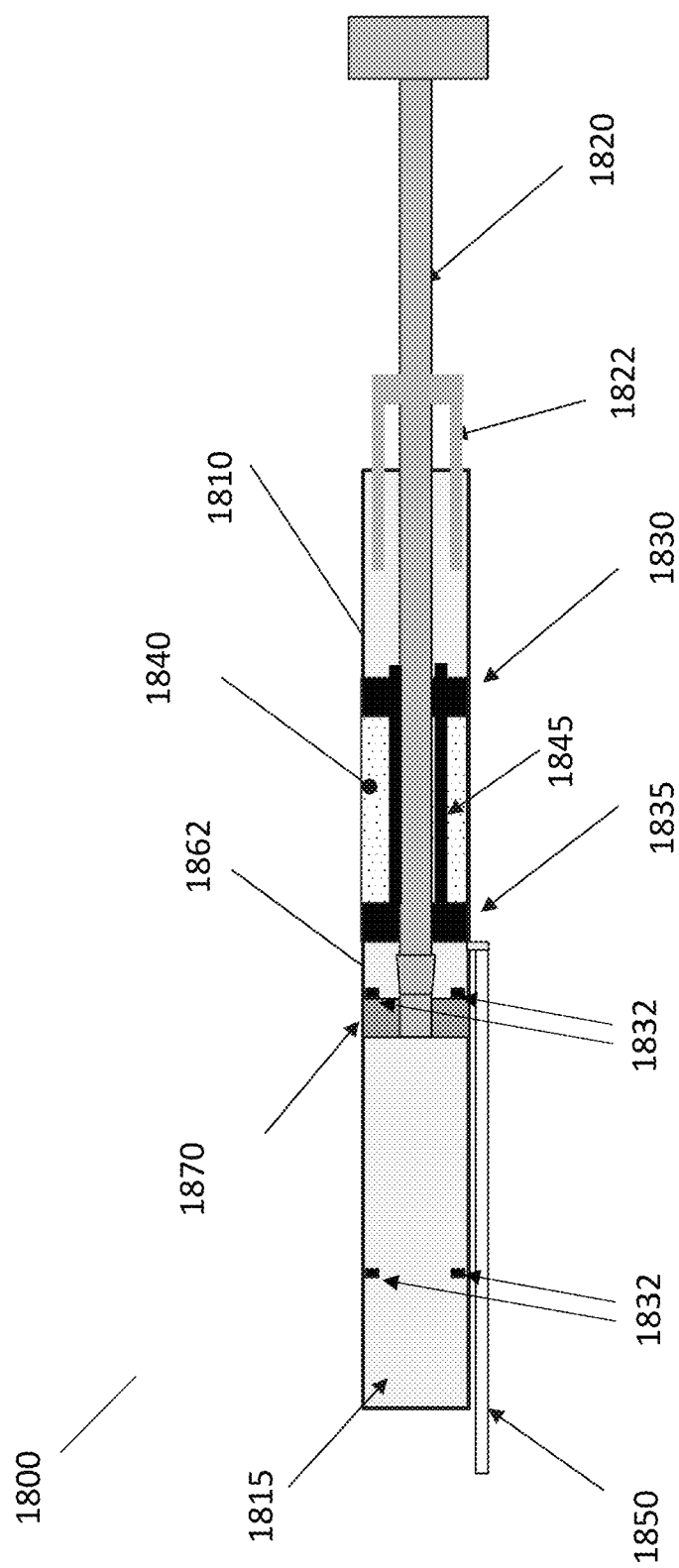
FIG. 13 is a cross-sectional side view of an exemplary intravitreal injection and sampling device, according to at least one embodiment of the present disclosure.

FIG. 13 is a cross-sectional side view of an exemplary intravitreal injection and sampling device 1800, in accordance with at least one embodiment of the present disclosure. The device 1800 includes a housing 1810 and a needle 1850 in fluid communication with the housing 1810 as shown. The device 1800 further includes a shaft 1820, tubular collar 1822, and a pull piston 1870 integrated together as a single piece. The device 1800 further includes a divider piston 1835, a push piston 1830, and a sleeve 1845. The sleeve 1845 encloses the shaft 1820, and together with the divider piston 1835 and push piston 1830 define a drug chamber 1840 within the housing 1810 used to contain liquid medicine as shown. The divider piston 1835 and pull piston 1870 define a chamber 1862 within the housing 1810 referred to as a sample chamber. The needle 1850 is in fluid communication with the volume between the pull piston 1870 and the divider piston 1835 as shown. The sleeve 1845 is not strictly required for the definition of the drug chamber 1840; however, it does prevent tiny amounts of drug from being carried down on the surface of the shaft 1820 from the drug chamber 1840 into the sample chamber during the operation of the device described below.

The operation of the device 1800 is explained in conjunction with FIGS. 14A-14E, which illustrate device 1800 at various points of operation, assuming the needle is inserted in an eye. FIG. 14A represents device 1800 in a starting position. FIG. 14B illustrates operation of the device 1800 as the shaft is moved in the direction shown. As the shaft is pushed further into the housing 1810, the movement of the shaft 1820 causes the pull piston 1870 to move accordingly within the housing 1810, thereby enlarging the sample chamber 1862 and creating negative pressure within the chamber 1862. The negative pressure causes a sample to flow from the eye through the needle 1850 and into the sample chamber 1862, thereby drawing a sample, such as vitreous, into the sample chamber 1862. The device 1800 is dimensioned to pull the desired sample volume from the eye. Floating pistons (divider piston 1835 and push piston 1830) remain in place until the tubular collar 1822 rests against the push piston 1830, because friction with the barrel 1815 is higher than friction by shaft 1820 plus atmospheric pressure multiplied by the area of the push piston 1830.

The tubular collar 1822 eventually comes into contact with the push piston 1830. At this point, a chamber switch occurs. As force is applied to the shaft 1820 to move it in the direction shown, a corresponding force is applied to the push piston 1830. The push piston 1830, sleeve 1845 and divider piston 1835 move in unison until the divider piston 1835 comes to rest against the hard stop 1832 for divider portions. At this point, illustrated in FIG. 14C, the needle 1850 is in fluid communication with the medicine chamber 1840. As force continues to be applied to the shaft 1820, the tubular collar 1822 applies a corresponding pressure against the push piston 1830, causing the push piston 1830 to move in the same direction within the barrel 1815, and decreasing the volume of the drug chamber 1840 and creating positive pressure within the drug chamber 1840, thereby causing the medicine to flow through the needle 1850 and into the eye. The expulsion of the medicine from the device 1800 is illustrated in FIG. 14D.

FIG. 14E illustrates how the biofluid may be extracted from the device 1800. The extraction may occur while the needle 1850 is still inserted in the eye or it may occur after the needle 1850 is removed from the eye. The shaft 1820 is pulled relative to the housing 1810, thereby pulling the pull piston 1870 within the barrel 1815 in the direction of shaft movement. A side port 1855 is opened, and movement of the pull piston 1870 as shown decreases the volume of the sample chamber 1862 thereby causing the biofluid sample to flow out of the housing 1810 through the side port 1855.

As will be readily appreciated by those having ordinary skill in the art after becoming familiar with the teachings herein, the intravitreal injection and sampling device permits equivalent volumes of material to be removed from and injected into the eye, such that TOP can be maintained at healthy levels while vitreous humor sampling and drug injection are performed with a single needle stick and a single plunger press. Accordingly, it can be seen that the intravitreal injection and sampling device fills a long-standing need in the art, by permitting a single needle stick to deliver one or more drugs into the eye and facilitate one or more biological tests to be performed on the vitreous humor, using manual procedures and workflows that simulate a single hypodermic injection.

A number of variations are possible on the examples and embodiments described above. For example, the needle may include a filter to sample from vitreous lacunae in aged eyes. A stabilizing grip relative to the needle and syringe may be included for a stable and comfortable grip. The intravitreal injection and sampling device may include a sensor or indicator to determine if a desired sample volume has been achieved. In some embodiments, the drug may be delivered and then the sample recovered into the original drug chamber, where position of needle is adjusted axially between delivery and sampling to avoid extracting the drug from the eye and thus reducing delivered dose. The sample chamber may contain one or more integrated bioassays (e.g., coated onto the interior of the syringe). The device may include a system for vitreous sampling without a vitreous cutter where a flushing solution exits the sampling ports in order to release possible vitreous strand capture or traction. A combined sampling/drug delivery needle device may include cold chain data recording for sample recording after acquisition or may include a stabilizer in the compartment of sample chamber for one or more known analytes. The sample chamber may include for example internal point-of-care analysis for expression levels of: VEGF, VEGFa-to-VEGFb ratio, Placental Derived Growth Factor, Inflammatory cytokines IL-6, IP-10, IL-8, ICAM-1, MCP-1, or residual drug levels. A retractable sheath may be included to provide shielding of the needle, both to prevent contamination and associated endophthalmitis, and also to make needle less scary to patients, therefore saving vision in first time shot recipients who might be tempted to delay the shot due to fear.

The intravitreal injection and sampling device may be part of a system for veterinary applications where many, relatively young, animals can be rapidly treated and sampled with minimal downtime for sterilization between drug deliveries. In some embodiments, the initiation of sample suction and drug release is triggered by the force on, or motion of, a needle-covering sheath pressed against the eye, or a stop indicating that needle has been inserted to a target depth in the eye by a button at the distal end of device. The intravitreal injection and sampling device may include a unique, optically readable tracking label to avoid interference with existing visual features of device.

Some embodiments may include one or more pinch valves comprising a flexible hose (e.g., Tygon tubing) pulled into a bind by a bi-stable cable actuator. Pinch valves may provide low cost, non-hermetic seals. Some embodiments may include an automatic hydraulic plunger drive, a spring pushing a hydraulic oil chamber, with an actuated valve and a restriction port to control flow rate. The intravitreal injection and sampling device may include a dual lumen bi-needle. For example, a 34 G needle for drug delivery can fit in lumen of a 27 G sampling needle with some extra space. In some embodiments, the needle tip position is extended or retracted by a distance of between 1 mm and 6 mm in between the injection and sampling steps.

The technology described herein may be employed in human medicine, veterinary medicine, agriculture, education, mechanics, or other fields where it is desirable to withdraw material and inject a comparable volume of replacement material, using a single needle stick and plunger press.

Accordingly, the logical operations making up the embodiments of the technology described herein are referred to variously as operations, steps, objects, elements, components, or modules. Furthermore, it should be understood that these may occur or be arranged or performed in any order, unless explicitly claimed otherwise or a specific order is inherently necessitated by the claim language.

All directional references e.g., upper, lower, inner, outer, upward, downward, left, right, lateral, front, back, top, bottom, above, below, vertical, horizontal, clockwise, counterclockwise, proximal, and distal are only used for identification purposes to aid the reader's understanding of the claimed subject matter, and do not create limitations, particularly as to the position, orientation, or use of the intravitreal injection and sampling device. Connection references, e.g., attached, coupled, connected, and joined are to be construed broadly and may include intermediate members between a collection of elements and relative movement between elements unless otherwise indicated. As such, connection references do not necessarily imply that two elements are directly connected and in fixed relation to each other. The term "or" shall be interpreted to mean "and/or"

rather than "exclusive or." Unless otherwise noted in the claims, stated values shall be interpreted as illustrative only and shall not be taken to be limiting.

The above specification, examples and data provide a complete description of the structure and use of exemplary embodiments of the intravitreal injection and sampling device as defined in the claims. Although various embodiments of the claimed subject matter have been described above with a certain degree of particularity, or with reference to one or more individual embodiments, those skilled in the art could make numerous alterations to the disclosed embodiments without departing from the spirit or scope of the claimed subject matter.

Still other embodiments are contemplated. It is intended that all matter contained in the above description and shown in the accompanying drawings shall be interpreted as illustrative only of particular embodiments and not limiting. Changes in detail or structure may be made without departing from the basic elements of the subject matter as defined in the following claims.

What is claimed is:

1. An injection and extraction ophthalmic device, comprising:
    a housing for receiving:
        an injectant chamber configured to store an injectant;
        a plunger disposed within the injectant chamber; and
        a stopper coupled to a distal portion of the plunger;
    a hypodermic needle disposed at a distal end of the housing; and
    a sample chamber located adjacent to the distal end of the housing, wherein the housing, the hypodermic needle, and the sample chamber are arranged such that:
        the sample chamber is configured to receive material via the hypodermic needle in response to movement of the stopper to a first depth within the housing; and
        when the stopper is moved to a second depth within the housing exceeding the first depth, the injectant chamber is configured to dispense the injectant through the hypodermic needle;
        wherein the sample chamber is configured to stop receiving any of the material when the injectant chamber is dispensing the injectant, and wherein the injectant chamber does not dispense any of the injectant when the sample chamber is receiving the material.

2. The device of claim 1, wherein the housing is a double-barreled syringe, and wherein the injectant chamber is disposed within a first barrel of the housing in fluid communication with the hypodermic needle, and the sample chamber is disposed within a second barrel of the housing in fluid communication with the hypodermic needle.

3. The device of claim 1, wherein moving the stopper to the first depth creates a volume of reduced pressure in the sample chamber, and wherein moving the stopper to the second depth creates a volume of increased pressure within the injectant chamber.

4. The device of claim 1, wherein the housing is a single-barreled housing, and wherein the sample chamber is disposed within the housing between the injectant chamber and the distal end.

5. The device of claim 4, wherein a pressure difference within the sample chamber relative to an exterior pressure is sufficient to draw material through the hypodermic needle into the sample chamber after the stopper is positioned at a first depth within the housing.

6. The device of claim 1, further comprising a test, pre-loaded into the sample chamber or in fluid communication with the sample chamber, that provides a visual indication of a property of the material.

7. The device of claim 1, wherein a volume of the injectant is substantially equal to a volume of the material.

8. The device of claim 1, wherein a volume of the injectant is in the range 0.01 milliliters (mL)-0.3 mL.

9. The device of claim 1, wherein the sample chamber includes a cooler or stabilizing chemical to stabilize the material for later analysis.

10. The device of claim 1, further comprising a unique human-readable or machine-readable ID associated with the device at time of manufacture.

11. The device of claim 1, further comprising a portion on the device that can be tagged with an identifier unique to a patient.

12. The device of claim 1, wherein a distal tip of the hypodermic needle is configured to be extended or retracted in the material by a distance of between 1 millimeter (mm) and 6 mm during an interval between the drawing of the material into the sample chamber, and the dispensing of the injectant from the injectant chamber.

13. The device of claim 1, further comprising a cutter incorporated onto the hypodermic needle.

14. The device of claim 1, wherein the device is further configured so that no material is received into the sample chamber via the hypodermic needle and no injectant is dispensed from the injectant chamber through the hypodermic needle when the stopper is moved to a third depth within the housing greater than the first depth but less than the second depth.

15. The device of claim 1, wherein the plunger is configured to move along a common centerline within the housing to the first depth and the second depth.

16. An injection and extraction ophthalmic device, comprising:
    a barrel comprising a chamber for receiving:
        a drug reservoir containing a liquid; and
        a plunger coupled to the drug reservoir;
    a needle coupled to a distal end of the barrel, the needle comprising a proximal portion and a distal portion, the proximal portion extending proximally within the barrel, and the distal portion extending distally from the barrel; and
    a sample container positioned adjacent the proximal portion of the needle; and
    wherein the barrel, the needle, and the sample container are configured such that:
        the needle is fluidly connected to the sample container in response to movement of the plunger to a first depth within the barrel; and when the plunger is moved to a second depth within the barrel exceeding the first depth, the drug reservoir is configured to dispense the liquid through the needle;
        wherein the sample chamber is configured to stop receiving any of the material when the injectant chamber is dispensing the injectant, and wherein the injectant chamber does not dispense any of the injectant when the sample chamber is receiving the material.

17. The device of claim 16, wherein the plunger is configured to move along a common centerline within the barrel to the first depth and the second depth.

* * * * *